US008729266B2

(12) United States Patent
Grote et al.

(10) Patent No.: US 8,729,266 B2
(45) Date of Patent: *May 20, 2014

(54) PREPARATION OF N-ALKYLATED OPIATES BY REDUCTIVE AMINATION

(75) Inventors: Christopher W. Grote, Webster Groves, MO (US); Brian Orr, O'Fallon, MO (US); Tao Jiang, St. Louis, MO (US); Gary L. Cantrell, Troy, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 423 days.

This patent is subject to a terminal disclaimer.

(21) Appl. No.: 12/668,900

(22) PCT Filed: Jun. 16, 2008

(86) PCT No.: PCT/US2008/067058
§ 371 (c)(1),
(2), (4) Date: Jan. 13, 2010

(87) PCT Pub. No.: WO2009/012005
PCT Pub. Date: Jan. 22, 2009

(65) Prior Publication Data
US 2010/0197921 A1 Aug. 5, 2010

Related U.S. Application Data

(60) Provisional application No. 60/950,127, filed on Jul. 17, 2007.

(51) Int. Cl.
*C07D 489/02* (2006.01)
(52) U.S. Cl.
CPC .................................. *C07D 489/02* (2013.01)
USPC ....................................................... 546/44
(58) Field of Classification Search
CPC .............................................. C07D 489/02
USPC ........................................................ 546/44
See application file for complete search history.

(56) References Cited

U.S. PATENT DOCUMENTS

| 2,772,270 | A | 11/1956 | Weiss |
| 3,332,950 | A | 7/1967 | Blumberg et al. |
| 3,717,643 | A | 2/1973 | Archer |
| 4,089,855 | A | 5/1978 | Chatterjie et al. |
| 4,443,605 | A | 4/1984 | Kotick et al. |
| 4,673,679 | A | 6/1987 | Aungst et al. |
| 4,775,759 | A | 10/1988 | Rice et al. |
| 4,795,813 | A | 1/1989 | Schwartz |
| 4,912,114 | A | 3/1990 | Revesz |
| 5,240,933 | A | 8/1993 | Merz et al. |
| 5,336,483 | A | 8/1994 | de Costa et al. |
| 5,668,285 | A | 9/1997 | Rice et al. |
| 5,693,820 | A | 12/1997 | Helmchen et al. |
| 5,756,745 | A | 5/1998 | Kavka |
| 5,847,142 | A | 12/1998 | Mudryk et al. |
| 6,184,381 | B1 | 2/2001 | Ikariya et al. |
| 6,509,467 | B1 | 1/2003 | Blacker et al. |
| 7,045,646 | B2 | 5/2006 | Tanis et al. |
| 2006/0014908 | A1 | 1/2006 | Rotermund et al. |
| 2006/0182692 | A1 | 8/2006 | Fishburn et al. |
| 2008/0009629 | A1 | 1/2008 | Avdagic et al. |
| 2008/0045715 | A1 | 2/2008 | Mitchell et al. |

FOREIGN PATENT DOCUMENTS

| EP | 0 034 480 | 8/1981 |
| EP | 0 879 823 | 11/1998 |
| JP | 2008-526694 | 7/2006 |
| WO | 97/20789 | 6/1997 |
| WO | WO 2004/085058 | 10/2004 |
| WO | WO 2005/100361 | 10/2005 |
| WO | WO 2006/035195 | * 4/2006 ........... C07D 489/08 |
| WO | WO 2006/052710 | 5/2006 |

OTHER PUBLICATIONS

March's Advanced Organic Chemistry, 5th ed., (2001), Chapter 16.*
Van Gurp et al., "Synthesis of 7,8-Didehydro-3,4-Dimethoxy . . . ", Bull. Soc. Chim. Belg., vol. 96/n° Apr. 1987, p. 325-329.
Uwai et al., "Syntheses and receptor-binding studies of derivatives . . . ", Bioorganic & Medicinal Chemistry, 12, 2004, p. 417-421, XP 002488979.
Malspeis et al., "Metabolic Reduction of Naltrexone I. Synthesis, Separation . . . ", Res. Commun. Chem. Pathol. Pharmacol, 2(43), 1975.
Olsen et al., "Conjugate Addition Ligands of Opioid Antagonists . . . ", J. Med. Chem., 1990, 33(2), p. 737-741.
Koolpe et al., "Opioid Agonists and Antagonists. 6-Desoxy-6-substituted . . . ", J. Med. Chem., 1985, 28(7), p. 949-957.
Fuiji et al., "Ruthenium(II)-Caatalyzed Asymmetric Transfer . . . ", J. Am. Chem. Soc., 1996, 118, p. 2521-2522.
Yamakawa et al., "The Methal-Ligand Bifunctional Catalysis: A Theoretical Study on . . . ", J. Am. Chem. Soc., 2000, 122, p. 1466-1478.
Uematsu et al., "Asymmetric Transfer Hydrogenation of Imines", J. Am. Chem. Soc., 1996, 118, p. 4916-4917.
Wu et al., "Asymmetric transfer hydrogenation of imines and iminiums . . . ", Chem. Commun., 2006, p. 1766-1768.
Mao et al., "A Chiral Rhodium Complex for Rapid Asymmetric Transfer . . . ", Organic Letters, 1999, vol. 1, No. 6, p. 841-843.
Uba et al., "Stereospecific Synthesis of Codeine . . . ", Chem. Pharm. Bull., vol. 27, Issue 9, 1979, p. 2257-2258.
Leland et al., "Analgesic narcotic antagonists. 5. 7,7-Dimethyldihydrocodeinones . . . ", J. Med. Chem.., 1981, 24, p. 717-721.

(Continued)

*Primary Examiner* — Robert Havlin

(57) ABSTRACT

The present invention is directed to the reduction of an N-imine moiety or a hemiaminal moiety of a morphinan in the presence of a ruthenium, rhodium, or iridium asymmetric catalyst and a hydrogen source.

18 Claims, No Drawings

(56) References Cited

OTHER PUBLICATIONS

Burke et al., "Probes for narcotic Receptor Mediated Phenomena . . . ", Heterocycles, vol. 23, No. 1, 1985, p. 99-110.
Sagara et al., "Specific Affinity Labeling of . . . ", Bioorganic & Medicinal Chemistry Letters, vol. 5, No. 15, 1995, p. 1609-1614.
Gao et al., "Synthesis of 7-Arylmorphinans . . . ", J. Med. Chem., 1998, 41, p. 3901-3098.
White et al., "Asymmetric Total Synthesis of (+)-Codeine via . . . ", J. Org. Chem., 1999, 64, p. 7871-7884.
Fuiji et al., "The First Example of the Stereoselective Synthesis of . . . ", Chem. Pharm. Bull., 52(6), 2004, p. 747-750.
Kalimin et al., "Palladium-Catalyzed 2-Phenylethenylation of Codeine . . . ", Helevetica Chimca Acta, vol. 89, 2006, p. 861-869.
Chatterjie et al., "Reduction of 6-Ketones of the Morphine Series . . . ", J. Org. Chem., vol. 41, No. 22, 1976, p. 3624-3625.
Brine et al., "Formamidinesulfinic Acid Reduction of Dihydrocodeinone Derivatives", J. Org. Chem., vol. 43, No. 8, 1978, p. 15551557.
De Costa et al., "Probes for Narcotic Receptor Mediated Phenomena . . . ", J. Med. Chem., 19972, 35, p. 2826-2835.
Olieman et al., "Conversion of (−)-dihydrocodeinone into . . . ", Laboratory of Organic chemistry Technische Hogeschool Delft, Julianalaan 136, Delft, The Netherlands, Mar. 15, 1976.
White et al., "Asymmetric Synthesis of (+)-Morphine . . . ", J. Org. Chem., 1997, 62, p. 5250-5251.
Borch et al., "The cyanohydridoborate Anion as a Selective Reducing Agent", Journal of the American Chemical Society, 93:12, Jun. 16, 1971, p. 2897-2904.
Abdel-Magid et al., "Reductive Animation of Aldehydes and Ketones . . . ", Tetrahedron Letters, vol. 31, No. 39, 1990, p. 5395-5598.
Gribble et al., "Reactions of Sodium Borohydride in Acidic Media . . . ", Communications, Aug. 1987, p. 709-711.
Campbell et al., "The Preparation of Unsymmetrical Secondary Aliphatic Amines", Jan. 1944, vol. 66, p. 82-84.
Seki, Studies on the Morphine Alkaloids . . . , vol. 84, No. 7, p. 626-631.
Hashiguchi et al., "Asymmetric Transfer Hydrogenation of Aromatic ketones Catalyzed by Chiral Ruthenium(II) Complexes", J. Am. Chem. Soc., vol. 177, No. 28, 1995, p. 7562-7563.
Palmer et al., "Asymmetric transfer hydrogenation of C=O and C=N bonds", Tetrahedron: Asymmetry 10, 1999, p. 2045-2061, XP 004174087.
Schellenberg, "The Synthesis of Secondary and Tertiary Amines by Borohydride Reduction", Nov. 1963, p. 3259-3261.
Spadoni et al., "2[$N$-Acylamino($C_1$-$C_3$)alkyl]indoles as $MT_1$ . . . ", J. Med. Chem., 1998, 41, p. 3624-3634.
Ohno et al., "Solid-Phase synthesis of 6-Sulfionylamino Morphinan Libraries", Synlett, 2002, No. 1, p. 93-96.
Lazar et al., "A Selective Removal of Benzyl Protecting Groups in Arylphosphate Esters with Bromotrimethylsilane", Synthetic Communications, 22(6), 1992, p. 923-931.
Butora et al., "Chemoenzymatic Synthesis of the Morphine Skeleton via Radical . . . ", Tetrahedron Letters, vol. 37, No. 45, 1996, p. 8155-8158.
Watanabe et al., "Novel Synthesis of the Ortho Ester Derivative of 4,5-Epoxymorphinan", Organic Letters, vol. 8, No. 3, 2006, p. 523-526.
Nagase et al., "The Facility of Formation of a $\Delta^6$ Bond in Dihydromorphinone and Related Opiates", J. Org. Chem., 1989, 54, p. 4120-4125.
"A New Reagent for the Selective, High-Yield N-Dealkylation of Teritary Amines: Improved Syntheses of Naltrexone and Nalbuphine", J. Org. Chem.., 1984, 49, p. 2081-2082.
Gorlitzer et al., "Diepoxy-bis-(iminoethano)-dinaphth[2,1-$b$:1',2'-$i$]acridine $^{2,3+}$)", Arch. Pharm. (Weinheim) 325, 1992, p. 637-641.
Lau et al., "Evolutiion of a Series of Non-Quinoline Leukotriene $D_4$ Receptor Antagonist . . . ", Bioorganic & Medicinal chemistry Letters, vol. 5, No. 15, 1995, p. 1615-1620.
Schmidhammer, "134. Synthesis and Biological ion of 14-Alkoxymorphinans Part $4^1$) Opioid Agonists and Partial Opioid Agonists in a Series of . . . ", Helevitca Chimca Acta, vol. 72, 1989, p. 1233-1239.
Bognar et al., Izvestiya po Khimiya, 1975, 81(1), p. 203-215.
Noyori et al., "Asymmetric Catalysts by Architechtural and Functional Molecular . . . ", Agew. Chem. Int., Ed. 2001, 40, p. 40-73.
Borch et al., "A New Method for the Methylation of Amines", J. Org. Chem., vol. 36, No. 10, 1972, pp. 1673-1674.
Noyori et al., "Asymmetric Transfer Hydrogenation Catalyzed by Chiral Ruthenium Complexes", Acc. Chem. Res., 1997, 30, 97-102.
Puntener et al., "New Efficient Catalysts for Enantioselective Transfer Hydrogenations", Tet. Lett., 1996, 37(45), 8165-8168.
Meuzelaar et al., "Chemistry of Opium Alkaloids, 45 Improvements in the Total Synthesis of Morphine", Eur. J. Org. Chem., 1999, 2315-2321.
March, Advanced Organic Chemistry, Wiley-Interscience, 1985, 3rd edition, pp. 798-799.

\* cited by examiner

PREPARATION OF N-ALKYLATED OPIATES BY REDUCTIVE AMINATION

CROSS REFERENCE TO RELATED APPLICATIONS

This application is a national stage application of PCT/US2008/0067058, filed Jun. 16, 2008, which claims the benefit of U.S. Provisional Application No. 60/950,127 filed Jul. 17, 2007.

FIELD OF THE INVENTION

The present invention generally relates to processes for the synthesis of intermediates or end product morphinans. More specifically, the invention is directed to the synthesis of N-alkylated opiates by reductive amination using asymmetric hydrogen transfer.

BACKGROUND OF THE INVENTION

N-alkylated morphinans are important pharmaceuticals, typically used as analgesics, opiate agonists, and antagonists. With the increasing use of these agents, a practical and effective method of preparation of these compounds is vital to synthesizing diverse N-alkyl substituted morphinans.

There are three main methods for preparing N-alkylated morphinans. In a first method, the morphinan nitrogen is alkylated by a $S_N2$ methodology using an alkyl halide (or other appropriate leaving group) in the presence of a base. Normally, mixtures of mono and dialkylated morphinans are obtained. The dialkylated morphinan typically results from over-alkylation on the nitrogen atom. In the case of opiates having a 3-phenolic group, alkylation of the 3-phenolic group also results. Complex isolations are normally employed to separate the mono-alkylated from the higher alkylated species. Accordingly, careful reaction conditions are necessary to prepare the mono-alkylated product in sufficient yield.

A second method for synthesizing N-alkylated morphinans consists of reductive alkylation. In this type of reaction, the free base of the amine is reacted with an aldehyde forming an imine or Schiff Base. Reduction of the Schiff Base is normally accomplished by the use of a hydride transfer agent. This methodology is generally known as "reductive alkylation". Normal reducing reagents for this reaction include borohydride reagents (e.g., sodium borohydride reagents, sodium cyanoborohydride), boranes, and aluminum hydride reagents (e.g., lithium aluminum hydride). See, for example, A. F. Abdel-Magid, et al., *Reductive Amination of Aldehydes and Ketones by Using Sodium Triacetoxyborohydride*, Tet. Lett. 31 (39), pp. 5595-98 (1990). These reagents need to be used in stoichiometric quantities to achieve complete reduction. Difficulties resulting from this synthetic method include the release of boron or aluminum salts from the product. Improved procedures have utilized metal catalytic methodology to achieve this reduction. See, for example, WO 2006/035195 (N. Goodwin, et al.). Hydrogen gas in the presence of a transition metal catalyst has also been used to achieve this reduction.

A third method for preparation of N-alkylated morphinans consists of an acylation reduction methodology. Typically, in this synthetic process, the amine is reacted with an acyl equivalent, then reduced using boranes or main group hydride species (e.g. lithium aluminum hydride). Careful control of reaction conditions must be observed to prevent hydrolysis of the acyl equivalent.

Thus, a need remains for a quick and effective synthetic method for the preparation of N-alkylated morphinans resulting in high yields

SUMMARY OF THE INVENTION

Among the various aspects of the present invention is the provision of a process for the preparation of N-alkylated morphinans. In particular, an N-imine moiety or a hemiaminal moiety of a morphinan is reduced in the presence of a ruthenium, rhodium, or iridium asymmetric catalyst and a hydrogen source. The resulting N-alkylated morphinan may then be derivatized, if desired, in one or more additional steps to form other morphinans.

Briefly, therefore, the present invention is directed to a process for the preparation of a N-alkylated morphinan (II) having the formula

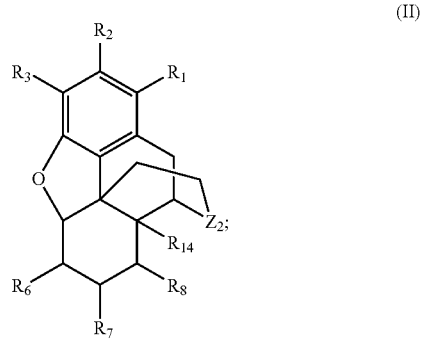

(II)

the process comprising reducing an N-imine morphinan or a hemiaminal moiety of a morphinan in the presence of a ruthenium, rhodium, or iridium asymmetric catalyst and a hydrogen source, the N-imine morphinan or the hemiaminal morphinan (I) having the formula:

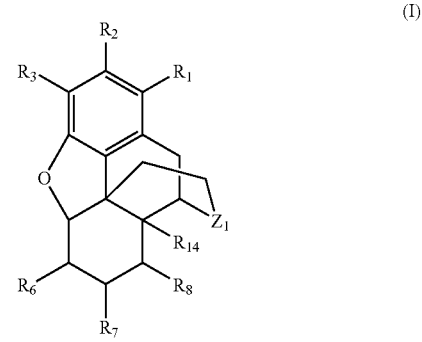

(I)

wherein $R_1$ is hydrogen, hydrocarbyl, substituted hydrocarbyl, halo, or —$OR_{111}$;

$R_2$ is hydrogen, hydrocarbyl, substituted hydrocarbyl, halo, or —$OR_{211}$;

$R_3$ is hydrogen, hydrocarbyl, substituted hydrocarbyl, or —$OR_{311}$;

$R_6$ is hydrogen, hydrocarbyl, substituted hydrocarbyl, or —$OR_{611}$ $R_7$ is hydrogen, hydrocarbyl, substituted hydrocarbyl, or —$OR_{711}$;

$R_8$ is hydrogen, hydrocarbyl, substituted hydrocarbyl, or —$OR_{811}$;

$R_{14}$ is hydrogen or hydroxy;

$R_{111}$ is hydrogen, hydrocarbyl, substituted hydrocarbyl, or a hydroxy protecting group;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{611}$ is hydrogen, hydrocarbyl, substituted hydrocarbyl, or a hydroxy protecting group;

$R_{711}$ is hydrogen, hydrocarbyl, substituted hydrocarbyl, or a hydroxy protecting group;

$R_{811}$ is hydrogen, hydrocarbyl, substituted hydrocarbyl, or a hydroxy protecting group;

$Z_1$ is >NCH(OH)($R_9$) or >$N^+$=CH($R_9$);

$Z_2$ is >$NCH_2(R_9)$; and $R_9$ is hydrogen, acyl, hydrocarbyl, substituted hydrocarbyl, or heterocyclo.

Other objects and features will be in part apparent and in part pointed out hereinafter.

DETAILED DESCRIPTION OF THE INVENTION

The present invention is directed to improved synthetic methods for the preparation of N-alkylated morphinans, salts, intermediates, and analogs thereof. In one aspect of the present invention, the synthetic methods utilize a ruthenium, rhodium, or iridium asymmetric homogeneous catalyst and a hydrogen source to reduce an N-imine moiety or a hemiaminal moiety of a morphinan (sometimes collectively referred to herein as the "N-imine/hemiaminal morphinan") to the corresponding alkyl group.

Morphinan Compounds

For purpose of discussion, the ring atoms of the morphinans of the present invention are numbered as follows. And within the core morphinan structure, there may be four chiral carbons, i.e., C-5, C-13, C-14, and C-9.

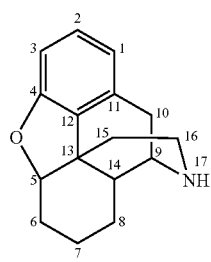

Further, for purposes of illustration, in relevant part, the N-imine and the hemiaminal moieties of the morphinans of the present invention correspond to Formulae (Ia) and (Ib), respectively:

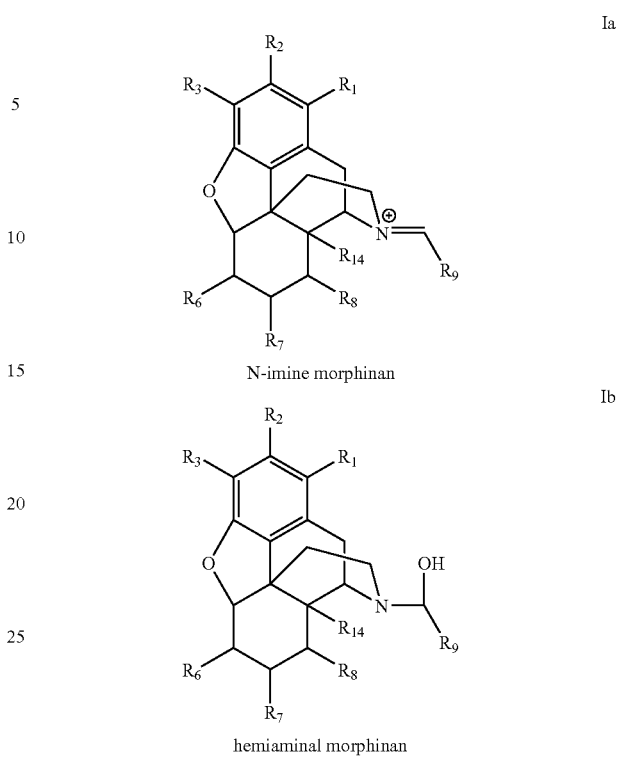

N-imine morphinan hemiaminal morphinan

In addition, as used herein, the symbol ">" is used in conjunction with the imine nitrogen atom and the hemiaminal nitrogen atom to represent the two covalent bonds that bind the nitrogen atom to the morphinan.

In one embodiment of the present invention, the morphinan corresponds to Formula (Ia), where $R_9$ is hydrogen, or substituted or unsubstituted $C_{1-8}$ alkyl, $C_{2-8}$ alkenyl, aryl, heterocyclo or acyl. Typical acyl groups include, but are not limited to, esters, amides, and carbamates. The optical activity, with respect to the rotation of polarized light, of the morphinan having Formula (Ia) may be (+) or (−). Furthermore, the configuration of the chiral carbons, C-5, C-13, C-14, and C-9, respectively, of the Formula (Ia) compound may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

In one example of this embodiment, $R_9$ is hydrogen, $C_{1-8}$ alkyl, $C_{2-8}$ alkenyl, aryl, heterocyclo, ester, amide, or carbamate. In a more restrictive example, $R_9$ is hydrogen, methyl, ethyl, propyl, cyclopropyl, cyclopropylmethyl, butyl, isobutyl, t-butyl, cyclobutyl, cyclobutylmethyl, methylcarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, cyclopropyl or cyclobutyl. In one preferred example, $R_9$ is cyclopropyl. In another preferred example, $R_9$ is cyclobutyl.

In another embodiment, the morphinan corresponds to Formula (Ib) wherein $Z_1$ is >NCH(OH)($R_9$) where $R_9$ is hydrogen, or substituted or unsubstituted $C_{1-8}$ alkyl, $C_{2-8}$ alkenyl, aryl, heterocyclo or acyl. Typical acyl groups include, but are not limited to, esters, amides, and carbamates. The optical activity of the morphinan having Formula (Ib) may be (+) or (−). In embodiments in which R$_9$ is hydrogen or hydroxy, the configuration of the chiral carbons, C-5, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule. In embodiments in which R$_9$ is not hydrogen or hydroxy, the carbon (C-18) attached to N-17 is also chiral, and thus, the configuration of C-5, C-13, C-14, C-9, and C-18, respectively, may be RRRRR, RRRRS, RRSRR, RRSRS, RRRSR, RRRSS, RRSSR, RRSSS, RSRRR, RSRRS, RSSRR, RSSRS, RSRSR, RSRSS, RSSSR, RSSSS, SRRRR, SRRRS, SRSRR, SRSRS, SRRSR, SRRSS, SRSSR, SRSSS, SSRRR, SSRRS, SSSRR, SSSRS, SSRSR, SSRSS, SSSSR, or SSSSS, provided that the C-15 and the C-16 carbons are both either on the alpha face of the molecule or the beta face of the molecule.

In one example of this embodiment, R$_9$ is hydrogen, C$_{1-8}$alkyl, C$_{2-8}$alkenyl, aryl, heterocyclo, ester, amide, or carbamate. In a more restrictive example, R$_9$ is hydrogen, methyl, ethyl, propyl, cyclopropyl, cyclopropylmethyl, butyl, isobutyl, t-butyl, cyclobutyl, cyclobutylmethyl, methylcarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, cyclopropyl or cyclobutyl. In one preferred example, R$_9$ is cyclopropyl. In another preferred example, R$_9$ is cyclobutyl.

For any of the above embodiments where the N-imine/hemiaminal morphinan corresponds to Formula (I) and Z$_1$ is >NCH(OH)(R$_9$) or >N$^+$=CH(R$_9$), R$_3$ is typically —OR$_{311}$ where R$_{311}$ is hydrogen, alkyl, acyl, alkaryl, aryl, or a hydroxy protecting group. In one example of this embodiment, R$_{311}$ is hydrogen, C$_{1-8}$ alkyl, aryl, C$_{1-8}$alkyl-C(O)—, aryl-C(O)—, C$_{1-8}$ alkyl-OC(O)—, or aryl-OC(O)—. In another example, R$_{311}$ is hydrogen or C$_{1-8}$ alkyl; preferably hydrogen or methyl. In a preferred example, R$_{311}$ is hydrogen.

In one embodiment in which the morphinan corresponds to Formula (I), R$_6$ is hydrogen, or substituted or unsubstituted C$_{1-8}$alkyl, C$_{2-8}$alkenyl, phenyl, or —OR$_{611}$. In one example of this embodiment, R$_6$ is —OR$_{611}$ where R$_{611}$ is C$_{1-8}$alkyl, C$_{2-8}$alkenyl, hydrogen or a hydroxy protecting group. In a more restrictive example, R$_{611}$ is methyl, ethyl, propyl, isopropyl, cyclopropyl, butyl, isobutyl, t-butyl, cyclobutyl, hydrogen, or a hydroxy protecting group; preferably, methyl, ethyl, hydrogen, or a hydroxy protecting group; more preferably, hydrogen or a hydroxy protecting group.

In another embodiment in which the morphinan corresponds to Formula (I), R$_1$, R$_2$, R$_6$, R$_7$, and R$_8$ are hydrogen. In an alternative embodiment, at least one of R$_1$, R$_2$, R$_6$, R$_7$, and R$_8$ is other than hydrogen; for example, R$_1$ may be hydrocarbyl, halo, or —OR$_{111}$ where R$_{111}$ is hydrogen, alkyl, acyl, alkaryl, aryl, or a hydroxy protecting group. In another example, R$_7$ is a substituted hydrocarbyl group; for example, 3,3-dimethylbutan-2-ol.

When a morphinan corresponding to Formula (I) is reduced in the presence of a ruthenium, rhodium, or iridium asymmetric catalyst and a hydrogen source in accordance with the process of the present invention, the resulting morphinan corresponds to Formula (II):

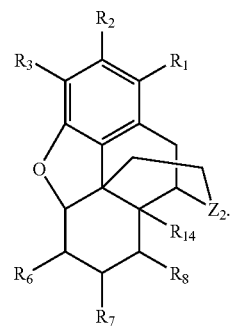

(II)

wherein R$_1$, R$_2$, R$_3$, R$_6$, R$_7$, R$_8$, R$_{11}$, and R$_{14}$ are as previously defined for Formula (I) and Z$_2$ is >NCH$_2$(R$_9$). The optical activity of the morphinan having Formula (II) may be (+) or (−), and the configuration of the chiral carbons, C-5, C-13, C-14, and C-9, respectively, may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

Exemplary morphinan (II) products include buprenorphine, 6-ketalnaltrexone, naltrexone, nalmefene, nalbuphine, and diprenorphine:

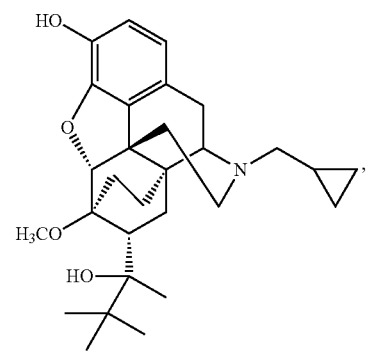

Buprenorphine

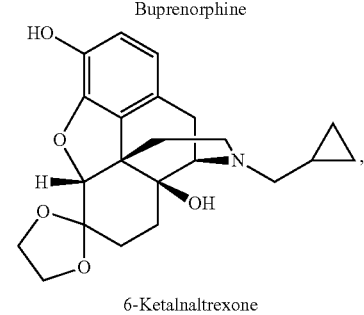

6-Ketalnaltrexone

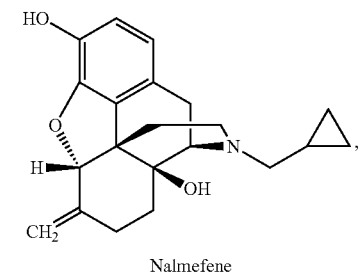

Nalmefene

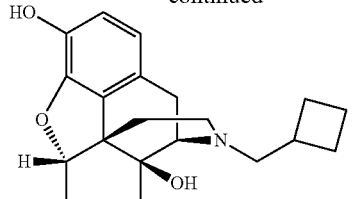

Nalbuphine

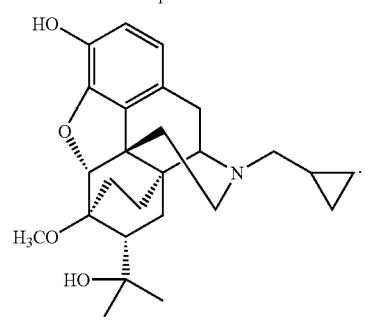

Diprenorphine

Ruthenium, Rhodium, or Iridium Asymmetric Catalysts

Generally, the ruthenium, rhodium, or iridium asymmetric catalyst of the present invention facilitate reductions of the hemiaminal ($Z_1$=>NCH(OH)($R_9$)) and/or the imine ($Z_1$=>$N^+$=CH($R_9$)) moieties. In general, these asymmetric catalysts comprise (a) a metal source consisting of a ruthenium complex, a rhodium complex, an iridium complex, or a combination thereof and (b) one or more chiral ligands. Typically, the ratio of metal to chiral ligand is about 1:1. In one example, the metal source is a ruthenium complex or a rhodium complex. In another example, the metal source is dichloro(arene)Ru(II) dimer, dichloro(pentamethylcyclopentadienyl)Rh(II) dimer, BINAP-Ru(II) diacetate, BINAP-Ru(II) dichloride, BINAP-Ru (II) dibromide, BINAP-Ru(II) diiodide, [RuCl((R or S)BINAP)($C_6H_6$)]Cl, or dichloro(pentamethylcyclopentadienyl)iridium (III) dimer.

Typically, the asymmetric catalysts of the present invention comprise ruthenium, rhodium, iridium, or a combination thereof complexed with bidentate, chiral ligands using nitrogen, oxygen, or phosphorous donor atoms as more fully described in, for example, U.S. Pat. No. 5,693,820 (Helmchen et al.) and R. Noyori et al., *Asymmetric Catalysts by Architectural and Functional Molecular Engineering: Practical Chemo- and Stereoselective Hydrogenation of Ketones*, Agew. Chem. Int. Ed. 2001, 40, pp. 40-73. These catalysts are sometimes referred to as Noyori catalysts. In one example, the chiral ligand of the present asymmetric catalysts corresponds to Formulae (670), (680), (690), or (700)

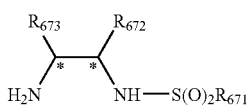

670

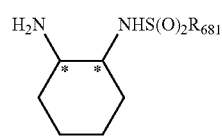

680

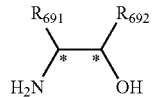

690

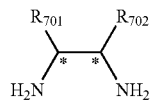

700 wherein $R_{671}$, $R_{672}$, $R_{673}$, $R_{681}$, $R_{691}$, $R_{692}$, $R_{701}$, and $R_{702}$ are independently alkyl or aryl and wherein $R_{691}$ and $R_{692}$ of Formula (690) and $R_{701}$ and $R_{702}$ of Formula (700), and the carbon atoms to which they are attached, may optionally form a cyclic or bicyclic compound. In the above structures, the "*" indicates a chiral carbon atom. The configuration of the chiral carbons of the asymmetric catalyst may be RR, RS, SR, or SS.

In one embodiment, the ligand corresponds to Formula (670) and $R_{672}$ and $R_{673}$ are each phenyl and $R_{671}$ is aryl. In another example of this embodiment, $R_{671}$ is tolyl, mesityl, or naphthyl. In an alternative embodiment, the ligand corresponds to Formula (680) and $R_{681}$ is tolyl, mesityl, 2,4,6-triisopropylphenyl, or naphthyl. In another example, the ligand corresponds to Formula (690) and $R_{691}$ and $R_{692}$ are hydrogen thus forming the compound, aminoethanol. In an alternative example, the ligand corresponds to Formula (690) and $R_{691}$ and $R_{692}$ are selected to form the following compound:

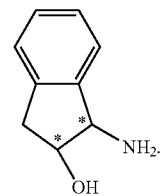

In another embodiment, the ligand corresponds to Formula (700) and $R_{701}$ and $R_{702}$ are hydrogen thus forming the compound, ethylenediamine.

In a preferred example, the ligand is (1S,2S)-(+)-N-4-toluenesulfonyl-1,2-diphenylethylene-1,2-diamine, (1R,2R)-(−)-N-4-toluenesulfonyl-1,2-diphenylethylene-1,2-diamine, dl-N-tosyl-1,2-diphenylethylenediamine, N-tosyl-1,2-diphenylethylenediamine, N-tosyl-1,2-ethylenediamine, or N-tosyl-1,2-diaminocyclohexane.

Examples of active ruthenium and rhodium asymmetric catalysts of the present invention include the following:

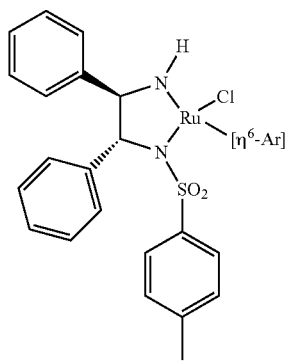

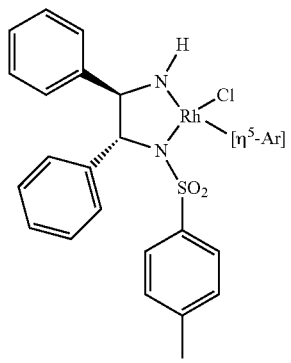

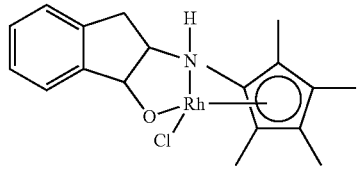

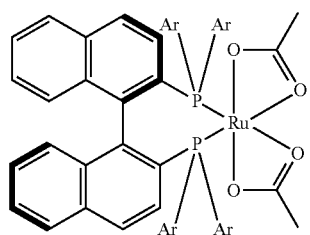

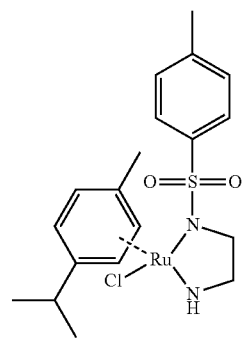

Chemical Formula: $C_{20}H_{29}ClN_2O_2RuS$
Exact mass: 498.1
Molecular Weight: 498

-continued

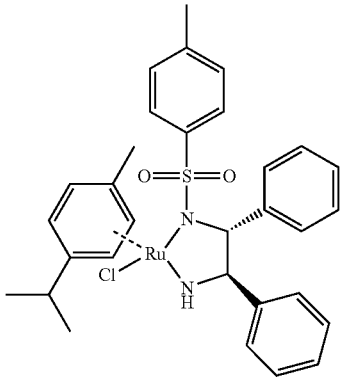

Chemical Formula: $C_{32}H_{37}ClN_2O_2RuS$
Exact mass: 650.1
Molecular Weight: 650.2

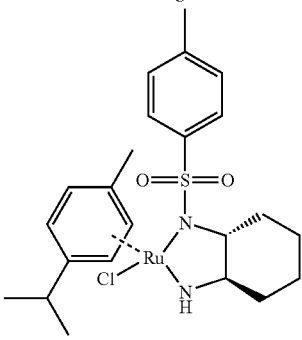

Chemical Formula: $C_{24}H_{35}ClN_2O_2RuS$
Exact mass: 552.1
Molecular Weight: 552.1

Hydrogen Source

The hydrogen source of the present process is any hydrogen source known to those skilled in the art. Methods of hydrogenation include in situ hydrogen transfer and high-pressure hydrogenation. In one example, the hydrogen source is hydrogen gas. To accomplish the reduction using this source, however, special reactors are required. On a preparative scale, this can poses safety challenges. An alternative to hydrogen gas is producing hydrogen in situ through hydrogen transfer methods. By producing the hydrogen source in situ, the pressures of standard hydrogenations (sometimes at 50 atms $H_2$) are avoided, thereby allowing for a safer preparation environment. Further, these reactions tend to be very mild. For example, using the hydrogen transfer methodology described, functional groups such as esters, amides, ethers, alkenes, and hydroxyls remain intact throughout the process.

Generally, the hydrogen source for the process of the present invention is, selected from isopropanol, formic acid, organic or inorganic salts of formic acid, or a combination thereof. In some instances, a small amount of base may be used to activate the catalyst. For example, in isopropanol, KOH is often used as an activator. In other examples, triethylamine may be used. In one example, the hydrogen source comprises an organic or inorganic salt of formic acid, preferably, the triethylamine salt of formic acid. In a preferred example, the hydrogen source is about a 5:2 mixture of formic acid to triethylamine.

Solvent

Typically, the solvent for the process of the present invention is selected from a nitrile (e.g., acetonitrile, propionnitrile), tetrahydrofuran (THF), an alcohol (e.g., methanol, ethanol, etc.), a halocarbon (e.g., a chloroalkyl such as dichloromethane, chloroform, 1,2-dichloroethane, or tetrachloroethylene), dimethylformamide (DMF), dimethylacetamide (DMAc), N-methylpyrrolidinone (NMP), an alkyl acetate (e.g., ethyl acetate or propyl acetate), toluene, or a combination thereof. In a more restrictive example, the solvent is acetonitrile, DMAc or a combination of acetonitrile and methanol.

Generally, the reaction of the present invention can be conducted at a temperature range from ambient temperature (~20° C.) to about 120° C. In one example, the reaction is carried out at temperature range of about 0° C. to about 80° C., preferably from about room temperature to about 40° C.

Imine/Hemiaminal Formation

Typically, the N-imine morphinan and the hemiaminal morphinan of the present invention are synthesized by reacting a nor-morphinan with an aldehyde having the formula, $R_9CHO$, as shown below:

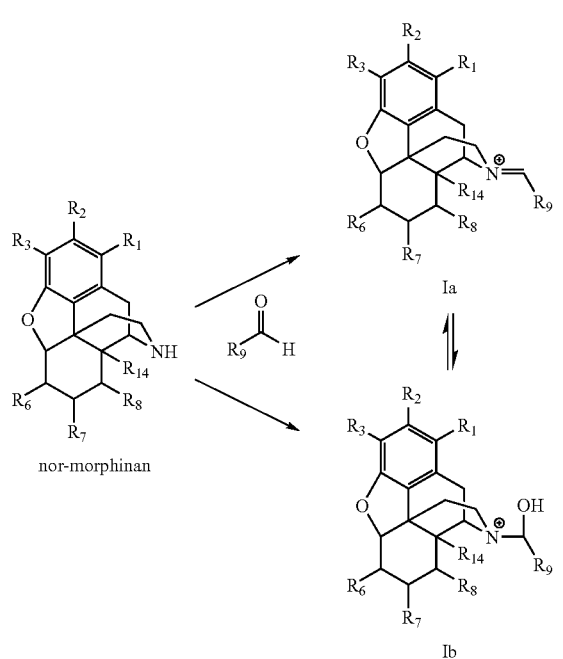

where $R_1$, $R_2$, $R_3$, $R_6$, $R_7$, $R_8$, $R_6$ and $R_{14}$, are as previously defined for morphinans corresponding to Formula (I). Upon formation, the N-imine morphinan (Ia) and the hemiaminal morphinan (Ib) form an equilibrium. The aldehyde is typically introduced in an amount ranging from about 1.0 to about 1.25 equivalents of aldehyde per equivalent of nor-morphinan. The solvent system for this step typically comprises an organic solvent, such as methanol, acetonitrile, toluene, ethyl acetate or a combination thereof. This reaction may be carried out, for example, at a temperature range of about room temperature (25° C.) to about reflux. Preferably, the reaction is carried out at about room temperature (25° C.) over a period of about 1 to about 5 hours, typically about 3 hours. An azeotropic distillation step may be added to increase the reaction rate of imine formation.

Formation of the N-Alkylated Morphinan

Once the formation of the N-imine morphinan (Ia) and the hemiaminal morphinan (Ib) is complete, the synthesis of the N-alkylated morphinan (II) can occur according to the following reaction scheme:

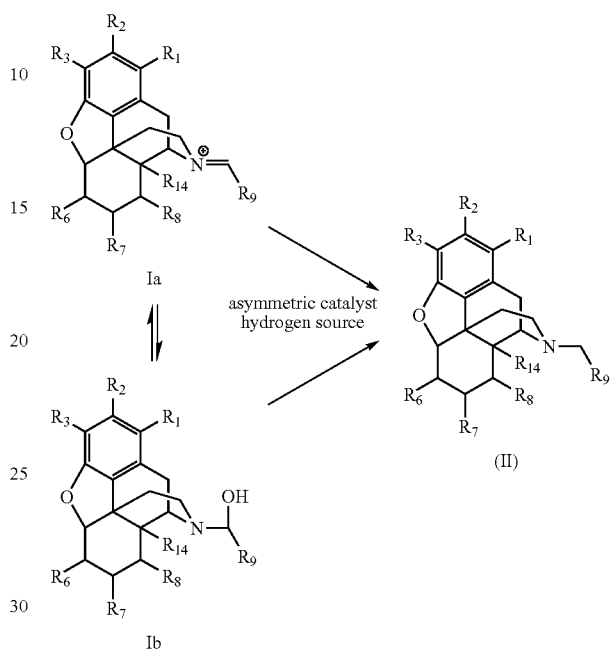

Typically, for this type of reaction, the N-imine morphinan (Ia) and the hemiaminal morphinan (Ib) are in equilibrium. When treated with a ruthenium, rhodium, or iridium asymmetric catalyst and a hydrogen source, as described herein, the N-imine moiety is converted to the corresponding tertiary amino group and the hydroxy group of the hemiaminal moiety is removed thereby forming the N-alkylated morphinan product (II). Without being bound to any particular theory, it is believed that the product (II) is predominantly, if not entirely, formed from the N-imine morphinan (Ia). It may be that the reduction of the N-imine morphinan to the product, coupled with the equilibrium formed with the hemiaminal morphinan, is the driving force behind the reaction. That is, the more N-imine morphinan is reduced to product, the more hemiaminal morphinan converts to the N-imine morphinan to maintain balance in the equilibrium. Sufficient evidence for this theory, however, is lacking. It is known, that when the mixture of N-imine and hemiaminal morphinans is reacted with a ruthenium, rhodium, or iridium asymmetric catalyst and a hydrogen source, the end product forms in high yield.

Generally, for the reduction of morphinans (Ia) and (Ib) to the product (II), the substrate to solvent ratio is from about 1:2 to about 1:20, preferably about 1:4 to about 1:5. The hydrogen source can be any of those previously discussed. In one preferred example, the hydrogen source is 1 to 5 equivalents of a 2:5 mixture of triethylamine to formic acid ($NEt_3/HCO_2H$), plus an additional equivalent to form a salt with the morphinan nitrogen, which increases solubility of the morphinan. Other salts that may be used include the methanesulfonate, acetate, and hydrochloride salt. These salts, however, may react at a slower rate. The catalyst is generally loaded at about a 1/50 to about a 1/1000 loading ratio on a molar basis. Typically, this reaction occurs in a temperature range of about room temperature to about 40° C. The more dilute the solvent, the longer the reaction time at room temperature.

In another typical example, the product (II) is further reacted to form the desired morphinan. For example, the product (II) may be reacted with an acid (e.g., formic acid) to remove a protecting group.

DEFINITIONS

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of Buprenorphine

The overall synthesis of buprenorphine from NOR-buprenorphine is depicted in the following reaction scheme:

NOR-Buprenorphine (3.67 g, 8.87 mmol) was added to acetonitrile (30 mL). Cyclopropanecarboxaldehyde (1.25 g, 17.84 mmol) was added and the slurry stirred for 1 hour at room temperature. At that time, a 5 to 2 mixture of 98% formic acid/triethylamine [prepared by adding 98% formic acid (5.34 g, 116 mmol) to triethylamine (4.70 g, 46.4 mmol)] in 10 mL of acetonitrile was added. Dichloro(p-cymene)ruthenium (II) dimer (27 mg) was added followed by (1S,2S)-(+)-N-tosyl-diphenylethylenediamine (32 mg). The reaction was purged by nitrogen gas for 30 minutes and became homogeneous after this time. A steady flow of nitrogen was allowed to pass over the reaction. The reaction was stirred for 36 hours at room temperature. Evaporation of the mixture produced a thick oil (5.34 g). 10 mL acetonitrile was added and stirred at room temperature for 1 hour, and a precipitate formed. The precipitate was removed by filtration and washed with 5 mL cold (5° C.) acetonitrile. The precipitate was dried yielding the title product (3.66 g, 88.5% yield). HPLC analysis indicated 99.02% buprenorphine.

Example 2

Synthesis of Naltrexone from Noroxymorphone

The overall synthesis of naltrexone from noroxymorphone is depicted in the following reaction scheme:

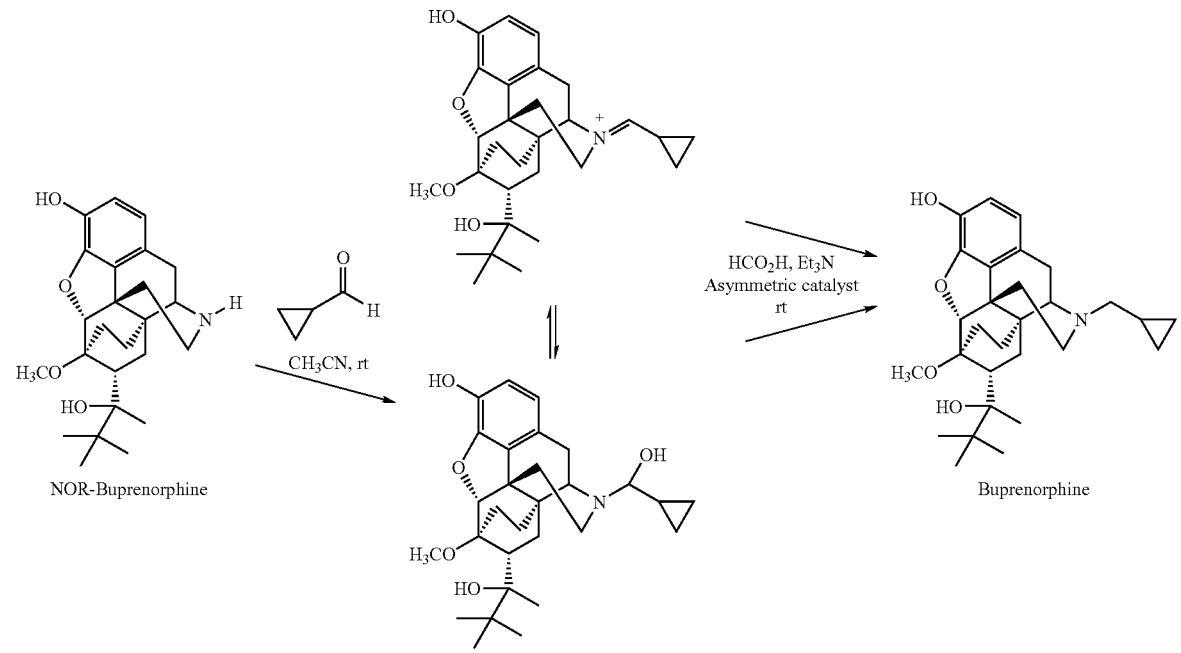

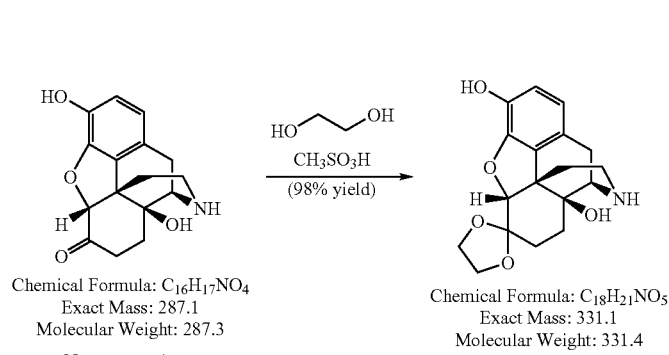

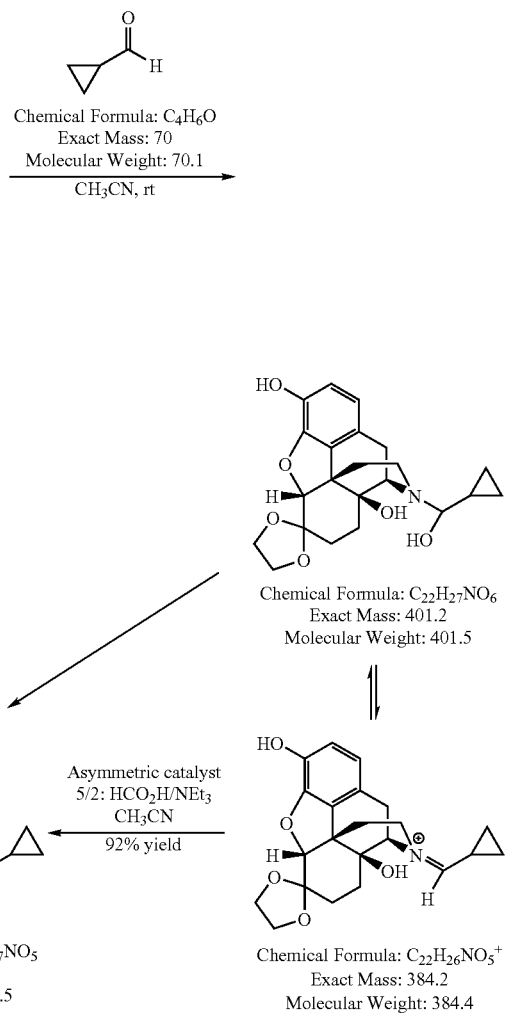

Example 2(a)

Synthesis of 6-Ketalnoroxymorphone from Noroxymorphone

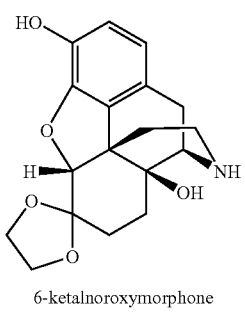 [SMILES: Oc1ccc2c3c1O[C@H]1C4(CC[C@@]5(O)[C@@H](C2)NCC[C@]315)OCCO4]

6-ketalnoroxymorphone

Noroxymorphone (3.30 g, 11.5 mmole) was slurried with ethylene glycol (14.26 g, 230 mmol, 12.85 mL). Methanesulfonic acid (2.21 g, 23.0 mmol, 1.49 mL) was then added dropwise. The reaction was allowed to stir overnight (16 h) at room temperature. Then, the reaction was poured slowly into 29% $NH_3/H_2O$ (50 mL) and stirred for 2 hours at room temperature where a white precipitate appeared. 6-Ketal Noroxymorphone (3.75 g, 98.5% yield) was isolated by filtration of the reaction mixture, washing the solid with distilled water (50 mL), and drying under reduced pressure (48 h, 25° C., 1 torr). HPLC analysis indicated 99.0% 6-ketalnoroxymorphone.

Example 2(b)

Synthesis of 6-Ketal Naltrexone from 6-Ketalnoroxymorphone

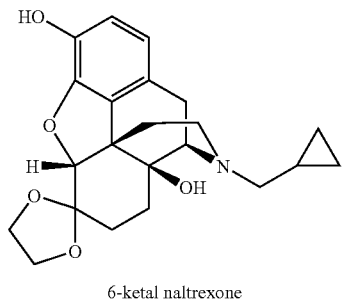 [SMILES: Oc1ccc2c3c1O[C@H]1C4(CC[C@@]5(O)[C@@H](C2)N(CC2CC2)CC[C@]315)OCCO4]

6-ketal naltrexone 6-ketalnoroxymorphone (0.95 g, 3.0 mmol), cyclopropanecarboxaldehyde (0.40 g, 6.0 mmol, 0.43 mL), and acetonitrile (5.0 mL) were combined and the slurry stirred for 2 hours at room temperature. The mixture was evaporated to dryness and dissolved in fresh acetonitrile (5.0 mL). At that time, a 5 to 2 mixture of 98% formic acid/triethylamine [prepared by adding 98% formic acid (1.78 g, 38.7 mmol, 1.46 mL) to triethylamine (1.45 g, 14.3 mmol, 2.0 mL)] in 10 mL of acetonitrile was added. Dichloro(p-cymene)ruthenium (II) dimer (19 mg) was added followed by (1S,2S)-(+)-N-tosyl-diphenylethylene diamine (26 mg). The reaction was purged by nitrogen gas (argon) for 30 minutes. After that, a flow of nitrogen was allowed to pass over the reaction. The reaction was stirred for 24 hours at room temperature. HPLC analysis indicated the reaction was complete. The reaction mixture was evaporated to a thick oil. To this thick slurry, fresh acetonitrile (5.0 mL) was added. After stirring at room temperature for 2 hours, a white solid formed. The precipitate was removed by filtration and washed with 5 mL cold (5° C.) acetonitrile. The precipitate was dried yielding the title product (1.06 g, 92% yield). HPLC analysis=99.0%.

Example 2(c)

Synthesis of Naltrexone from 6-ketal Naltrexone

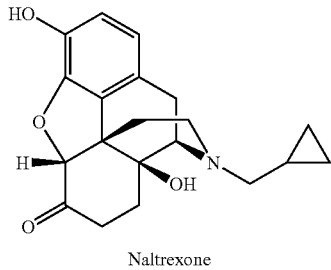 [SMILES: O=C1CC[C@@]2(O)[C@H]3Cc4ccc(O)c5c4[C@@]2(CCN3CC2CC2)[C@H]1O5]

Naltrexone 6-ketal naltrexone (1.06 g, 2.76 mmol) was added to a stirred solution of 88% $HCO_2H$ (5.0 mL) and distilled water (1.0 mL). After stirring for 2 hours at room temperature, the reaction was complete. The reaction mixture was slowly added to 30 mL 29% $NH_3/H_2O$, and a white precipitate formed. The white precipitate was isolated by filtration, washed with distilled water (5.0 mL), and dried yielding naltrexone (895 mg, 95% yield). HPLC analysis=99.0%.

What is claimed is:
1. A process for the preparation of a N-alkylated morphinan (II) having the formula

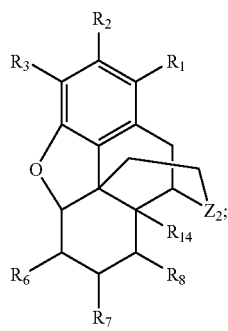

the process comprising reducing an N-imine morphinan or hemiaminal morphinan in the presence of an asymmetric catalyst and a hydrogen source, wherein the asymmetric catalyst comprises a dichloro(arene)Ru(II) dimer and a N-tosyl-diphenylethylenediamine ligand, the N-imine morphinan or hemiaminal morphinan (I) having the formula:

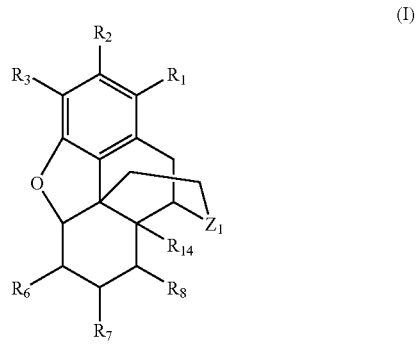

wherein
$R_1$ is hydrogen, hydrocarbyl, substituted hydrocarbyl, halo, or $-OR_{111}$;
$R_2$ is hydrogen, hydrocarbyl, substituted hydrocarbyl, halo, or $-OR_{211}$;
$R_3$ is hydrogen, hydrocarbyl, substituted hydrocarbyl, or $-OR_{311}$;
$R_6$ is hydrogen, hydrocarbyl, substituted hydrocarbyl, or $-OR_{611}$;
$R_7$ is hydrogen, hydrocarbyl, substituted hydrocarbyl, or $-OR_{711}$;
$R_8$ is hydrogen, hydrocarbyl, substituted hydrocarbyl, or $-OR_{811}$;
$R_{14}$ is hydrogen or hydroxy;
$R_{111}$ is hydrogen, hydrocarbyl, substituted hydrocarbyl, or a hydroxy protecting group;
$R_{211}$ is hydrogen, hydrocarbyl, substituted hydrocarbyl, or a hydroxy protecting group;
$R_{311}$ is hydrogen, hydrocarbyl, substituted hydrocarbyl, or a hydroxy protecting group;
$R_{611}$ is hydrogen, hydrocarbyl, substituted hydrocarbyl, or a hydroxy protecting group;
$R_{711}$ is hydrogen, hydrocarbyl, substituted hydrocarbyl, or a hydroxy protecting group;
$R_{811}$ is hydrogen, hydrocarbyl, substituted hydrocarbyl, or a hydroxy protecting group;
$Z_1$ is >NCH(OH)($R_9$) or >$N^+$=CH($R_9$);
$Z_2$ is >NCH$_2$($R_9$); and
$R_9$ is hydrogen, acyl, hydrocarbyl, substituted hydrocarbyl, or heterocyclo.

2. The process of claim 1, wherein the hydrogen source is isopropanol, formic acid, organic or inorganic salts of formic acid, or a combination thereof.

3. The process of claim 1, wherein the process occurs in a solvent selected from the group consisting of a nitrile, tetrahydrofuran (THF), an alcohol, a halocarbon, dimethylformamide (DMF), dimethylacetamide (DMAc), N-methylpyrrolidinone (NMP), an alkyl acetate, toluene or a combination thereof.

4. The process of claim 1, wherein:
$R_1$ is hydrogen or $-OR_{111}$;
$R_{111}$ is hydrogen, alkyl, acyl, alkaryl, aryl, or a hydroxy protecting group;
$R_2$ is hydrogen or $-OR_{211}$;
$R_{211}$ is hydrogen, alkyl, acyl, alkaryl, aryl, or a hydroxy protecting group;
$R_3$ is hydrogen or $-OR_{311}$;

R₃₁₁ is hydrogen, alkyl, acyl, alkaryl, aryl, or a hydroxy protecting group;

R₆ is hydrogen, or substituted or unsubstituted C₁₋₈ alkyl, C₂₋₈ alkenyl, phenyl, or —OR₆₁₁; and R₆₁₁ is C₁₋₈ alkyl, C₂₋₈ alkenyl, hydrogen or a hydroxy protecting group.

5. The process of 1, wherein:

R₁ is hydrogen;

R₂ is hydrogen;

R₃ is —OR₃₁₁;

R₃₁₁ is hydrogen or C₁₋₈ alkyl;

Z₁ is >NCH(OH)(R₉) or >N⁺=CH(R₉); and

R₉ is methyl, ethyl, propyl, isopropyl, cyclopropyl, butyl, isobutyl, t-butyl, cyclobutyl, pentyl or cyclopentyl.

6. The process of claim 1, wherein the N-alkylated morphinan (II) is buprenorphine:

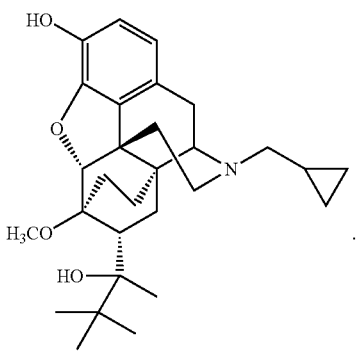 [SMILES: CO[C@]12CC[C@@]3(C[C@@H]1C(C)(O)C(C)(C)C)C1Cc4ccc(O)c5c4[C@@]3(CCN1CC1CC1)[C@H]2O5 ; "."]

7. The process of claim 1, wherein the process occurs within a temperature range of about 20° C. to about 40° C.

8. The process of claim 1, wherein the hemiaminal morphinan (I) is prepared from a normorphinan (X) having the formula:

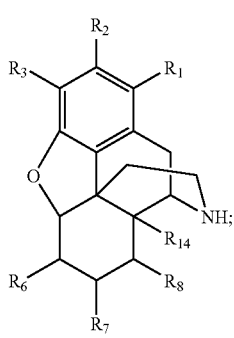

the process comprising reacting the nor-morphinan (X) with an aldehyde of the formula CH(O)R_g in a solvent to form the hemiaminal morphinan (I) having the formula:

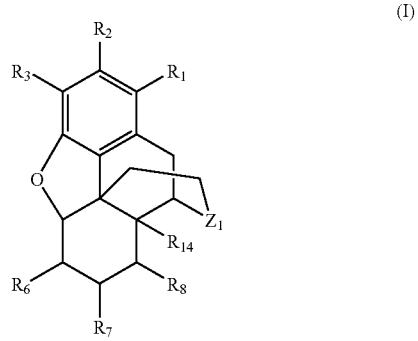

wherein

Z₁ is >NCH(OH)(R₉); and

R₉ is hydrocarbyl, acyl, substituted hydrocarbyl, or heterocyclo.

9. The process of claim 8, wherein the hemiaminal morphinan is in equilibrium with the corresponding N-imine morphinan, the hemiaminal having a >NCH(OH)(R₉) moiety for Z₁ and the N-imine morphinan having a >N⁺=CH(R₉) moiety for Z₁.

10. The process of claim 9, wherein:

R₃ is —OR₃₁₁;

R₃₁₁ is hydrogen;

R₆ is —OR₆₁₁;

R₆₁₁ is methyl;

R₇ is substituted alkyl or 3,3-dimethylbutan-2-ol; and

R₉ is cyclopropyl.

11. The process of claim 9, wherein the reaction occurs at about room temperature, and the solvent is acetonitrile.

12. The process of claim 9, wherein the nor-morphinan (X) is Nor-buprenorphine.

13. The process of claim 1, wherein the hemiaminal morphinan (I) is prepared by reacting a 6-keto nor-morphinan having the Formula (XI):

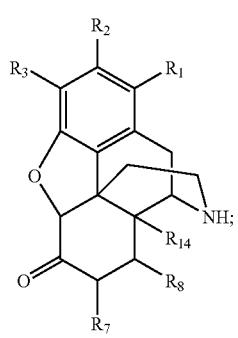

with ethylene glycol and an acid to form a 6-ketal nor-morphinan having the Formula (XII):

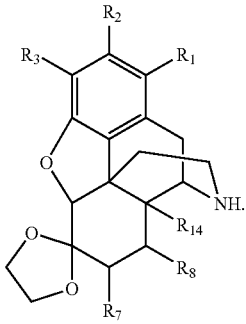

(XII)

14. The process of claim 13, wherein the acid is methanesulfonic acid.

15. The process of claim 13, wherein the 6-keto nor-morphinan (XI) is noroxymorphone and the 6-ketal nor-morphinan (XII) is 6-ketalnoroxymorphone.

16. The process of claim 15, wherein the 6-keto nor-morphinan (XII) is further reacted with an aldehyde of the formula $CH(O)R_9$ in a solvent to form the hemiaminal morphinan (I) having the formula:

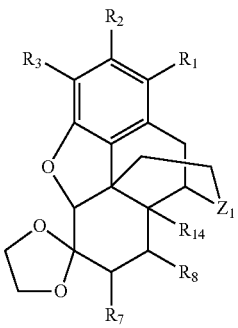

(I)

wherein
$Z_1$ is >NCH(OH)($R_9$); and
$R_9$ is hydrocarbyl, acyl, substituted hydrocarbyl, or heterocycle.

17. The process of claim 16, wherein the hemiaminal morphinan is in equilibrium with the corresponding N-imine morphinan, the hemiaminal morphinan having a >NCH(OH)($R_9$) moiety for $Z_1$ and the N-imine morphinan having a >N$^+$=CH($R_9$) moiety for $Z_1$.

18. The process of claim 17, wherein:
$R_3$ is —$OR_{311}$:
$R_{311}$ is hydrogen;
$R_9$ is cyclopropyl;
the reaction occurs at about room temperature; and
the solvent is acetonitrile.

* * * * *